(12) United States Patent
Miller et al.

(10) Patent No.: US 8,231,669 B2
(45) Date of Patent: Jul. 31, 2012

(54) TETHER GUIDED STENT SIDE BRANCH

(75) Inventors: Matthew J. Miller, Stillwater, MN (US);
Graig L. Kveen, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1627 days.

(21) Appl. No.: 11/232,682

(22) Filed: Sep. 22, 2005

(65) Prior Publication Data

US 2007/0067019 A1    Mar. 22, 2007

(51) Int. Cl.
*A61F 2/86* (2006.01)
(52) U.S. Cl. ............... 623/1.35; 623/1.12; 623/1.32
(58) Field of Classification Search .......... 623/1.35, 623/1.11, 1.15, 1.16, 1.12, 1.18, 1.2, 1.3, 623/1.32, 1.33, 1.34
See application file for complete search history.

(56) References Cited

U.S. PATENT DOCUMENTS

| | | | |
|---|---|---|---|
| 5,019,085 A | 5/1991 | Hillstead | 623/1.11 |
| 6,273,909 B1 * | 8/2001 | Kugler et al. | 623/1.13 |
| 6,293,967 B1 * | 9/2001 | Shanley | 623/1.15 |
| 6,352,553 B1 | 3/2002 | Van der Burg et al. | 623/1.11 |
| 6,379,308 B1 | 4/2002 | Brockway et al. | 600/486 |
| 6,416,540 B1 | 7/2002 | Mathur | 623/1.15 |
| 6,695,877 B2 | 2/2004 | Brucker | 623/1.16 |
| 6,716,238 B2 | 4/2004 | Elliott | 623/1.11 |
| 2001/0016766 A1 | 8/2001 | Vardi | 623/1.11 |
| 2002/0042650 A1 | 4/2002 | Vardi | 623/1.35 |
| 2002/0193873 A1 * | 12/2002 | Brucker et al. | 623/1.35 |
| 2004/0138737 A1 | 7/2004 | Davidson | 623/1.35 |
| 2005/0015108 A1 | 1/2005 | Williams et al. | 606/194 |

FOREIGN PATENT DOCUMENTS

| | | |
|---|---|---|
| WO | 2004/026180 A2 | 4/2004 |
| WO | 2005/009295 A1 | 2/2005 |

* cited by examiner

*Primary Examiner* — William H. Matthews
*Assistant Examiner* — Suba Ganesan
(74) *Attorney, Agent, or Firm* — Vidas, Arrett & Steinkraus

(57) ABSTRACT

A tether guided bifurcated stent having a generally tubular main body extending along a longitudinal axis connected to a side branch assembly. Both the main stent body and the side branch assembly are capable of forming an unexpanded configuration and an expanded configuration. The bifurcation's expansion is facilitated by a force exerted by the tether. When the side branch assembly is expanded it forms a secondary tubular region defining a generally tubular shape extending at an angle to the longitudinal axis of the main tubular body.

20 Claims, 8 Drawing Sheets

TETHER GUIDED STENT SIDE BRANCH

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent, restrained in a radially compressed configuration by a sheath or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven braids.

Within the vasculature however it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

This invention contemplates a number of embodiments where any one, any combination of some, or all of the embodiments can be incorporated into a stent and/or a stent delivery system and/or a method of use.

At least one embodiment of the invention is directed to a stent containing a tether guided side branch in which when the stent expands, a tether acts on the structural members of the side branch assuring that the side branch opens away from the main fluid lumen of the stent body and forms a second fluid lumen.

At least one embodiment of the invention is directed to a stent containing a tether guided side branch in which the tether acts upon the side branch, so that the longitudinal axis of the side branch forms an angle oblique to the longitudinal axis of the stent.

At least one embodiment of the invention is directed to a stent containing a tether guided side branch in which there are two or more side branches in fluid communication with the main stent body.

At least one embodiment of the invention is directed to a stent containing a flap type side branch. The flap(s) can be of any number of shapes including triangles, squares or rectangles, and when unexpanded, can lie adjacent to each other or can overlap. The flaps can be expanded by the same mechanism that expands the stent or it can utilize additional balloons or be pulled open by wires.

At least one embodiment of the invention is directed to a stent having a flap type side branch includes one or more tether lines which assure that when the stent expands, the side branch expands away from the main fluid lumen of the stent body and forms a second fluid lumen.

At least one embodiment of the invention is directed to a bifurcated stent having a substantially tubular primary body defining a circumferential plane, an outer surface, a primary lumen and having a primary longitudinal axis extending therethrough. The primary body is expandable from an unexpanded state to an expanded state and has a smaller diameter in the unexpanded state. The stent also has a primary body and a side branch assembly which comprises a substantially tubular secondary body defining a secondary lumen in fluid communication with the primary lumen having a secondary longitudinal axis forming an oblique angle with the primary longitudinal axis in the expanded state. The stent also has at least one tether, the at least one tether having a first end, a second end and a length therebetween, the first end engaged to the primary body and a second end engaged to the secondary body. In the unexpanded state, at least a portion of the tether length extends along the circumferential plane of the primary body. In the expanded state, at least a portion of the length of the tether moves to form an angle with the circumferential plane of the primary body that is greater than zero.

At least one embodiment of the invention is directed to stent in which the side branch assembly is constructed of a plurality of interconnected angled members disposed about an opening in the main stent body, where the interconnected angled members and the opening define a visibly recognizable petal pattern arrangement.

At least one embodiment of the invention is directed to stent in which the side branch assembly is constructed of a plurality of interconnected flap members wherein adjacent members are disposed about an opening in the main stent body, where the interconnected flap members and opening define a visibly recognizable flap pattern arrangement.

At least one embodiment of the invention is directed to a stent containing a tether guided side branch in which the side branch is formed out of a plurality of members configured in a petal arrangement about the side branch opening.

At least one embodiment of the invention is directed to a stent in which the flaps are comprised of a framework of struts.

At least one embodiment of the invention is directed to a stent in which the flaps are in a geometrically desirable shape which scaffolds the side branch lumen.

At least one embodiment of the invention is directed to a stent in which the flaps are laser cut.

At least one embodiment of the invention is directed to stent in which the flaps are triangular.

At least one embodiment of the invention is directed to stent in which the flaps are rectangular.

At least one embodiment of the invention is directed to stent in which the flaps are quadrilateral.

At least one embodiment of the invention is directed to stent in which the flaps when in an unexpanded state overlap.

At least one embodiment of the invention is directed to stent in which the oblique angle is about 90 degrees.

At least one embodiment of the invention is directed to stent in which a balloon assists the tether in adjusting the side branch assembly into its expanded state.

At least one embodiment of the invention is directed to stent in which at least one curved member is self expanding.

At least one embodiment of the invention is directed to stent in which at least one flap member is self expanding.

At least one embodiment of the invention is directed to stent in which the main tubular body of the stent further comprises struts, at least some portion which have a greater thickness than others.

At least one embodiment of the invention is directed to stent in which the main tubular body of the stent comprises struts, at least some portion which are more flexible than others.

At least one embodiment of the invention is directed to stent in which at least some portions of the curved members have a greater thickness than others.

At least one embodiment of the invention is directed to stent in which at least some portion of the curved members are more flexible than others.

At least one embodiment of the invention is directed to stent in which at least some portion of at least one flap member has a greater thickness than others.

At least one embodiment of the invention is directed to stent where at least some portion of at least one flap member has is more flexible than others.

At least one embodiment of the invention is directed to stent in which the flap members when in the unexpanded state completely cover the opening.

At least one embodiment of the invention is directed to stent in which the curved members when in the unexpanded state completely cover the opening.

At least one embodiment of the invention is directed to a method of treating a medical condition comprising the steps of: providing a reinforced bifurcated stent, the bifurcated stent comprising: a substantially tubular primary body defining a circumferential plane, an outer surface, a primary lumen and having a primary longitudinal axis extending therethrough, the primary body being expandable from an unexpanded state to an expanded state, wherein in the unexpanded state the primary body has a diameter less than that of the diameter in the expanded state, the primary body comprising a side branch assembly, in the expanded state the side branch assembly comprises a substantially tubular secondary body defining a secondary lumen having a secondary longitudinal axis extending therethrough, the secondary lumen being in fluid communication with the primary lumen, the secondary longitudinal axis forming an oblique angle with the primary longitudinal axis; and at least one tether, the at least one tether having a first end, a second end and a length therebetween, the first end engaged to the primary body and a second end engaged to the secondary body, in the unexpanded state, at least a portion of the tether length extending along the circumferential plane of the primary body, in the expanded state at least a portion of the length of the tether moved to a position defining a vector which forms an angle greater than zero with the circumferential plane of the primary body; positioning the stent in a location in a body; and deploying the stent.

BRIEF DESCRIPTION OF THE SEVERAL VIEWS OF THE DRAWINGS

The invention is best understood from the following detailed description when read in connection with accompanying drawings, in which.

DETAILED DESCRIPTION OF THE INVENTION

Figure 1:
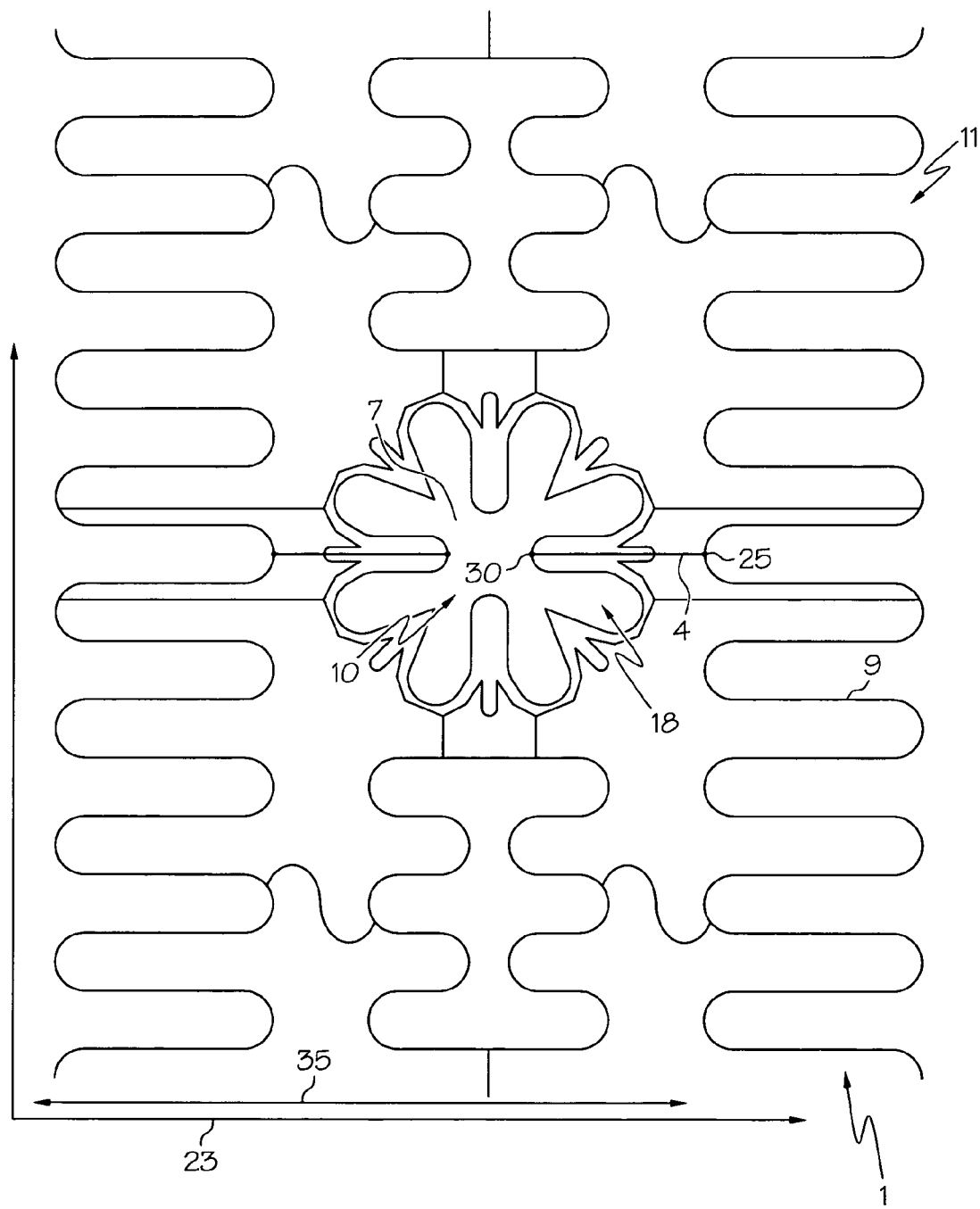
FIG. 1 is a lateral perspective image of an unexpanded tether guided petal-type bifurcated stent.

The invention will next be illustrated with reference to the figures wherein the same numbers indicate similar elements in all figures. Such figures are intended to be illustrative rather than limiting and are included herewith to facilitate the explanation of the apparatus of the present invention.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

In at least one embodiment of the invention, an example of which is shown in FIG. 1, a bifurcated stent (1) is shown. The stent comprises two portions, a primary tubular stent body (11) and a secondary body which forms a side branch assembly (10). The stent has an expanded and unexpanded state and when unexpanded, the secondary body covers at least a portion of the primary stent body as well as an opening in the primary stent body. FIG. 1 shows the stent (1) is shown in an unexpanded state, and shows the primary tubular stent body (11) connected to the side branch assembly (10). The primary stent body defines a circumferential plane (23) and in the unexpanded state the side branch assembly (10) generally lies along the circumferential plane (23).

The primary stent body (11) is comprised of a plurality of adjacent interconnected struts, or other stent members (9) that are arranged in any configuration or pattern desired. In at least one embodiment, such as in the embodiment depicted in FIG. 1, the members (9) are arranged in adjacent bands. When the stent (1) is expanded from a radially compressed state to a radially expanded state, the relative and/or configuration of the adjacent stent members (9) will be altered.

The side branch assembly (10) is surrounded by stent members (9) and is engaged to at least one of the stent members (9) of the primary stent body (11). The side branch assembly (10) comprises plurality of interconnected branch members (18) disposed about an opening (7) in the primary stent body (11). In the unexpanded state, the branch members (18) are positioned within the circumferential plane (23) of the primary stent body (11). When the stent (1) expands, the main stent body (11) forms a primary lumen (40) (as shown in FIG. 3) and the members (18) of the side branch (10) extend outward from the main stent body to form a secondary lumen (41) at an angle to the longitudinal axis (35) of the primary tubular body (which runs from the distal to the proximal end of the stent).

The extension of the side branch (10) is facilitated by a tether (4). This tether (4) spans between a first tether end (25) connected to the primary stent body (1) and a second tether end (30) connected to the side branch assembly (10). When the primary stent body (11) expands, the struts of the primary stent body (9) straighten or otherwise alter their shape/configuration to accommodate expansion of the stent body (11). This alteration impels the position of the first tether end (25) on the main stent body to move away from the member (18) where the second tether end (30) is located. The presence of the tether however, harnesses these positional changes in position to effectively 'pull' upon the member (18) out of the circumferential plane (23) of the primary stent body (1) and to form the walls of the side branch assembly (10) which defines the secondary fluid lumen. The pull of the tether (4) assures that the side branch (10) expands away from the main stent body (11) and forms a secondary fluid lumen in fluid communication with the primary lumen of the main stent body (11). The longitudinal axis of the side branch lumen is oriented at an oblique angle relative to the longitudinal axis of the main stent lumen. For the purposes of this application, the term "oblique" refers to an angle of greater than zero degrees, such as an angle between about 1 and about 180 degrees. In the context of this application, an oblique angle explicitly includes angles of or about 90 degrees. The tethers could be constructed out of a variety of materials including metals, polymers, and composites and can be either rigid or flexible. The tethers may also consist of multiple fibers arranged or braided together to form a cable like configuration.

Figure 2:
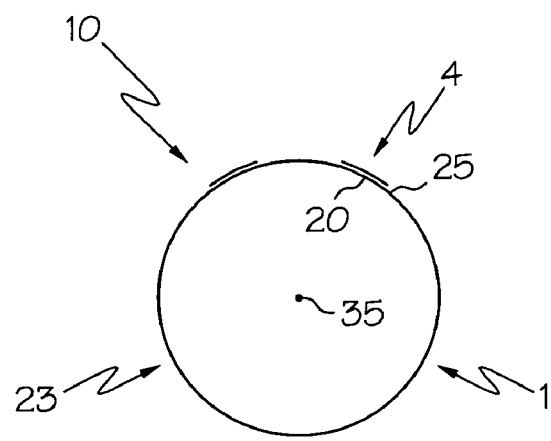
FIG. 2 is a cross sectional side perspective image of an unexpanded tether guided petal-type bifurcated stent.
Figure 3:
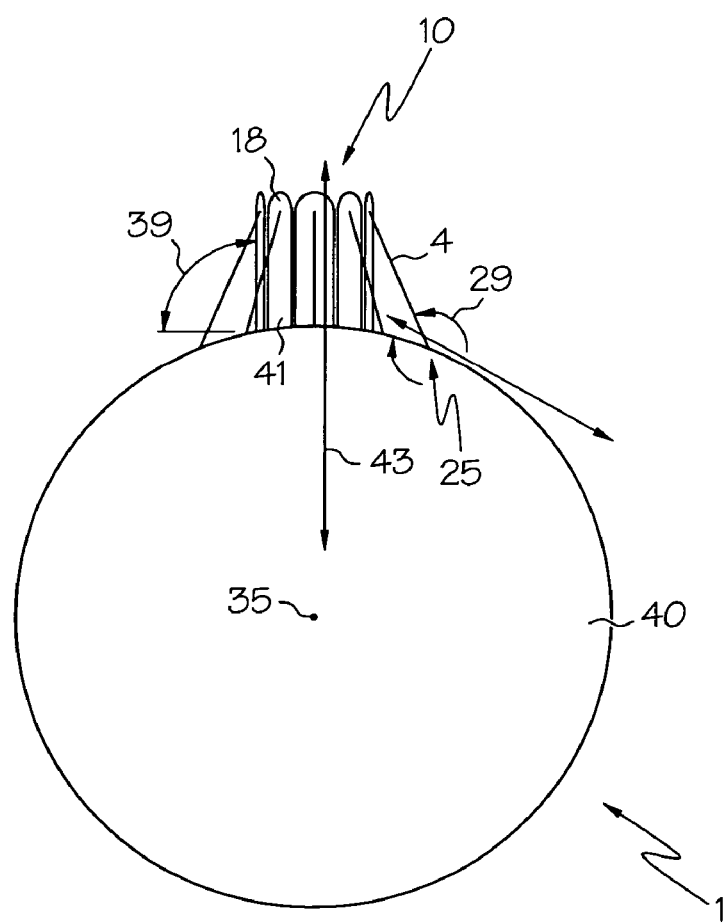
FIG. 3 is a cross sectional side perspective image of an expanded tether guided bifurcated stent demonstrating how the tethers assure proper deployment of the bifurcation.

As shown in FIG. 3 when the stent (1) is expanded to a radially expanded state, the branch members (18) are configured to bend, pivot or otherwise "open" outward away from the primary stent body (11) to more fully expose the side branch opening (7). When opened, the branch members (18) define a second fluid lumen (41) in fluid communication with the primary lumen (40) and which is directed along a second longitudinal axis (43). The second longitudinal axis (43) forms an oblique angle with the primary longitudinal axis (35) of the main stent body (11). The branch members (18) themselves also form oblique angles (39) relative to the circumferential plane which is facilitated by being pulled by the tethers (4) as the primary stent body (11) expands. The pulling also causes the tethers (4) to rise above the circumferential plane (23) and form an oblique angle (39) to line formed by the tangent of the circumferential plane at the position of the first tether end (25). By positioning the tether properly in the unexpanded state (for example in FIG. 2 by positioning the tether (4) slightly above the side branch members (18)) the tether will pull on the side branch member assuring it opens away from the main body of the stent. FIG. 3 illustrates how the tethers (4) restrain the side branch members (18) from expanding in any undesirable direction such as into the main lumen of the primary stent body (1). This invention encompasses all known methods of utilizing tethers or fibers to bias the allowed movements of a member with pulling tension.

In some embodiments tethers (4) are not configured to fully deploy the side branch assembly (10), but are utilized in conjunction with one or more other expansion mechanisms, such as an expansion balloon, or to aid in the deployment of a self-expanding side branch (10). In at least one embodiment, the tethers operate as the sole expansion mechanism of the side branch (10). The tethers can also allow for expansion of a side branch in an extreme angular direction not easily accomplished by either self expansion or a balloon because it provides lateral force in a direction that balloon or self expansion mechanism cannot easily facilitate. In addition, by selectively increasing branch member (18) or stent member (9) thickness, the bifurcation can be provided greater support or flexibility respectively. Combining the added support or flexibility characteristics with the expansion capability of a tether (4) allows for designing of a highly versatile stent. The stent can also comprise more than one side branch assembly and more than one kind of side branch assembly.

The tethers (4) can also be constructed out of a material with at least some rigidity so that they facilitate forming the secondary lumen by pushing the side branch away from the primary tubular region. In this embodiment, the tether would be placed on a stent member (9) of the main stent body (11). The tether can be placed on any location on the stent member (9). These tethers could function as push rods and could move towards the center of the side branch assembly, away from the center of the side branch assembly, or maintain its distance from the center of the side branch assembly in order to facilitate the desired side branch assembly expansion.

The functioning of this invention can be better understood by reference to a petal, an iris, and a crown. For purposes of this application the term "petal" refers to one or more side branch members (18) capable of twisting, bending, pivoting or otherwise opening to form a secondary lumen (41) by opening away from the circumferential plane (23) of the primary stent body (11). These petals can be arranged in an iris configuration when the stent (1) is unexpanded. For purposes of this application the term "iris" refers to one or more petals generally lying along the circumferential plane (23) of the stent (1) in the unexpanded configuration and covering at least a portion of the side branch opening (7). When the stent (1) assumes an expanded state, the petals assume a crown configuration. For purposes of this application the term "crown" which is defined as at least one petal lying at an oblique angle above the circumferential plane (23) of the primary stent body (11).

Figure 4:
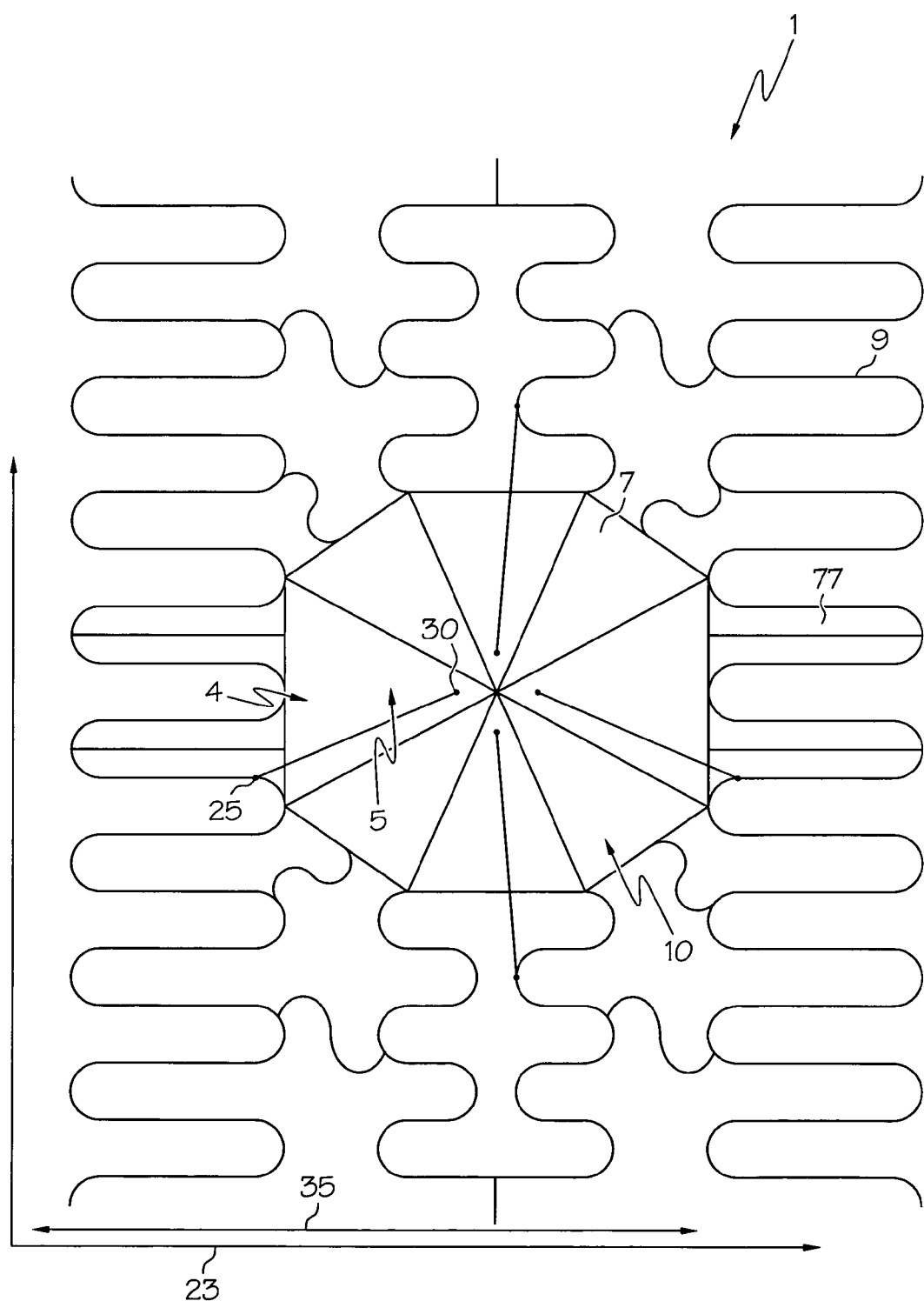
FIG. 4 is a lateral perspective image of an unexpanded tether guided triangular flap type bifurcated stent.

Referring now to FIG. 4 there is shown an embodiment of the invention in which the members of the side branch assembly (10) are configured as flaps (5). When the stent (1) is unexpanded, the flaps can overlap or blanket the side branch opening when in an iris configuration and when the stent (1) is expanded, the flaps can assume a crown configuration. These flaps (5) are capable of forming a second fluid lumen when the flaps open. In the illustration shown, the flaps (5) are provided with a substantially triangular or pie shape. The flaps (5) are pivotally engaged relative to the portion of the primary stent body (11) to which they are engaged and are capable of pivoting to form an oblique angle with the circumferential plane (23). In some embodiments, the flaps can be engaged to the primary stent body (11) by one or more connectors (77). These connectors (77) can be flexible or rigid and allow the flaps to pivot and form oblique angles to the circumferential plane (23). The tethers (4) are engaged to the triangular flaps by their first end and are engaged to the primary stent body (1) at the second end. When extended, these flaps (5) are pulled away from the primary tubular body of the primary stent body (1) by the tether (4) in the same manner as the petals shown in FIG. 3 and form a secondary fluid lumen.

In some embodiments, flaps (5) are portions of the primary stent body (1) which are cut, etched, molded or otherwise provided for from the tube, sheet or wires(s) from which the stent is manufactured. In at least one embodiment the flaps (5), which make up the side branch assembly (10) and may be characterized as struts or other stent members which have a different shape than the stent members of the primary stent body (1). For example, the flaps (5) which are shown in FIG. 4 have a substantially triangular planar shape where as the adjacent stent members have substantially rectangular planar shape.

Flap type side branch assemblies can be in any number of shapes including but not limited to triangles, squares, rectangles, circles, trapezoids or any other geometric shape. The side branch can be created by one or more flaps which have been expanded outward and away from one another about the opening of the side branch assembly (10). Flaps can also be combined with other types of side branch assemblies. Flaps can lie next to each other, can be apart, or when unexpanded can form a contiguous or overlapping "blanket" over the area of the side branch assembly (10). Some of these permutations can be seen in FIG. 5 where there is shown an embodiment of the invention in which the unexpanded side branch assembly (10) is in the shape of a rectangular flap (6). In this particular illustration the two rectangular flaps overlap but this is not a required feature. These flaps are also guided by tension from tethers (4).

Figure 5:
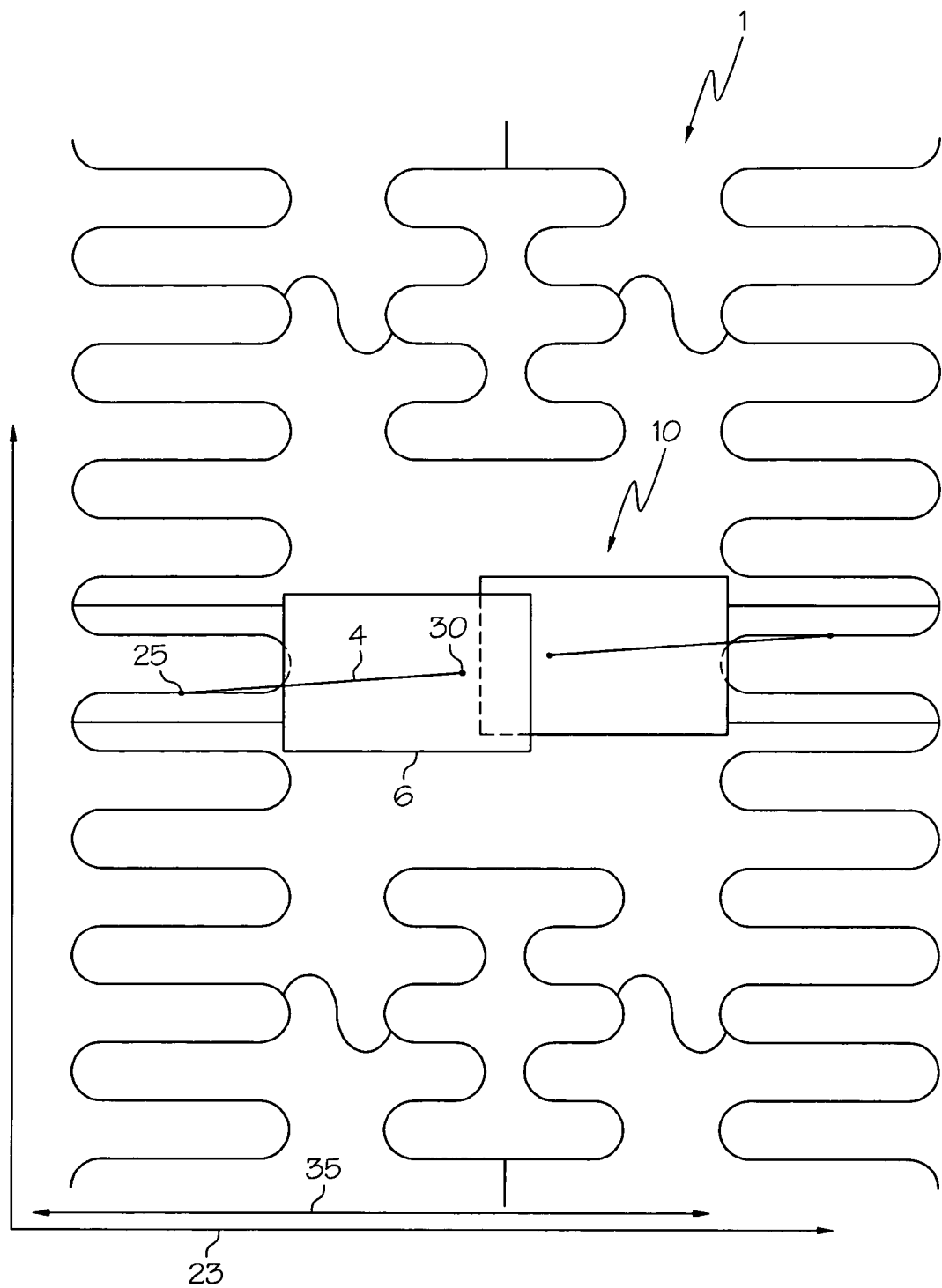
FIG. 5 is a lateral perspective image of an unexpanded tether guided overlapping rectangular type bifurcated stent.

The deployment of either branching member or flap type side branch assemblies do not interfere with the expansion of the stent (1) to its desired expanded configuration. FIGS. 4 and 5 are simple examples showing the basic embodiments and are not intended to exhaustively illustrate every possible application of the invention.

Figure 6:
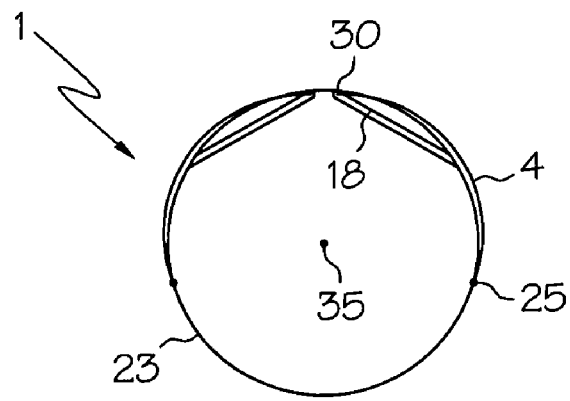
FIG. 6 is a cross sectional side perspective image of an unexpanded tether guided petal-type bifurcated stent.
Figure 7:
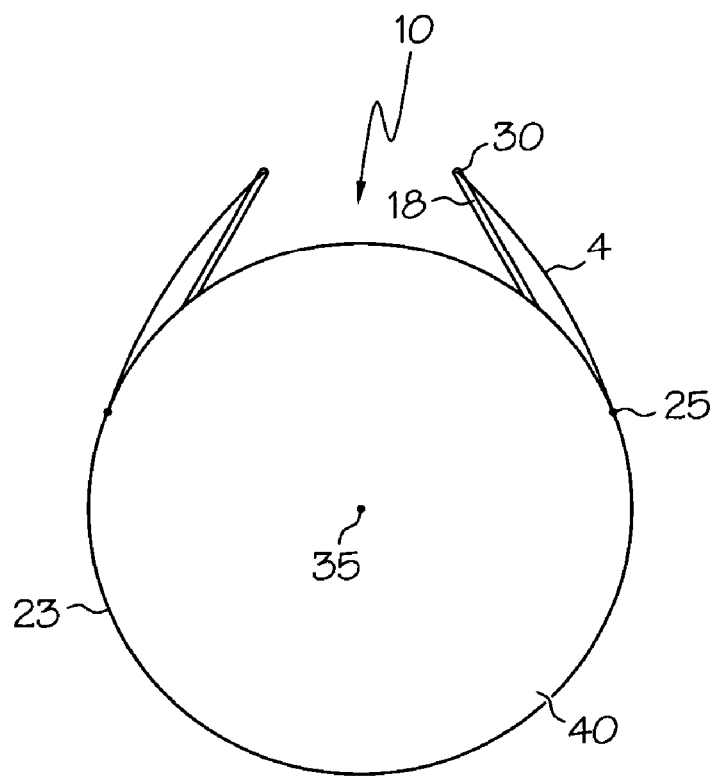
FIG. 7 is a cross sectional side perspective image of an expanding tether guided petal-type bifurcated stent.
Figure 8:
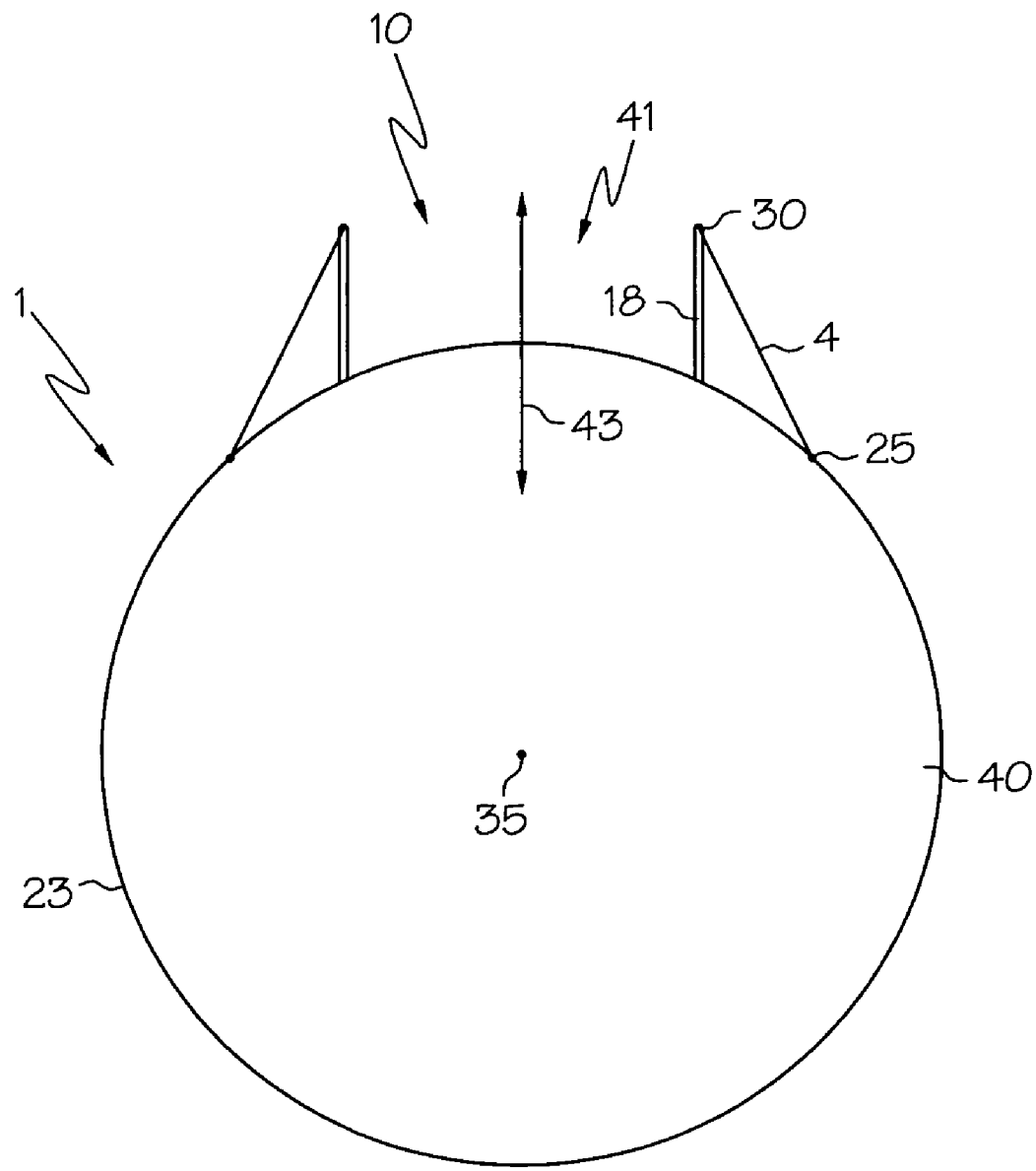
FIG. 8 is a cross sectional side perspective image of an expanded tether guided petal-type bifurcated stent.

Referring now to FIGS. 6, 7, and 8 there are shown embodiments of the invention in the unexpanded state (FIG. 6), in a transitional state (FIG. 7) and in an expanded state (FIG. 8). In FIG. 6, the stent (1) is unexpanded and the tethers (4) and the branch members (18) are positioned substantially along the circumferential plane (23) of the primary stent body (11). The tethers may also be positioned below the circumferential plane (23) or within the primary lumen (40) of the stent (1) when unexpanded. In FIG. 7, the primary stent body (11) and the primary lumen (40) have increased their perimeter. This in turn has caused the branch members (18) to be pulled out of the circumferential plane (23) by tension from the tethers (4) because the expanded perimeter has moved the first end of the tether (25) further away from the side branch assembly (10). Although FIG. 7 illustrates the transitional state with a particular shape and geometry, the device is not limited to this shape and geometry and can assume a number of shapes and configurations while expanding.

In FIG. 8, the stent (1) has completely assumed its expanded state. The side branch members (18) have been pulled by the tethers (4) to form a secondary lumen (41) in fluid communication with the primary lumen (40). The secondary lumen (41) is projecting away from the circumferential plane (23) of the primary stent body (11). In some possible embodiments, the tethers are constructed out of absorbable, bio-degradable, or bio-absorbable materials, and after expansion are dissolved away.

Figure 9:
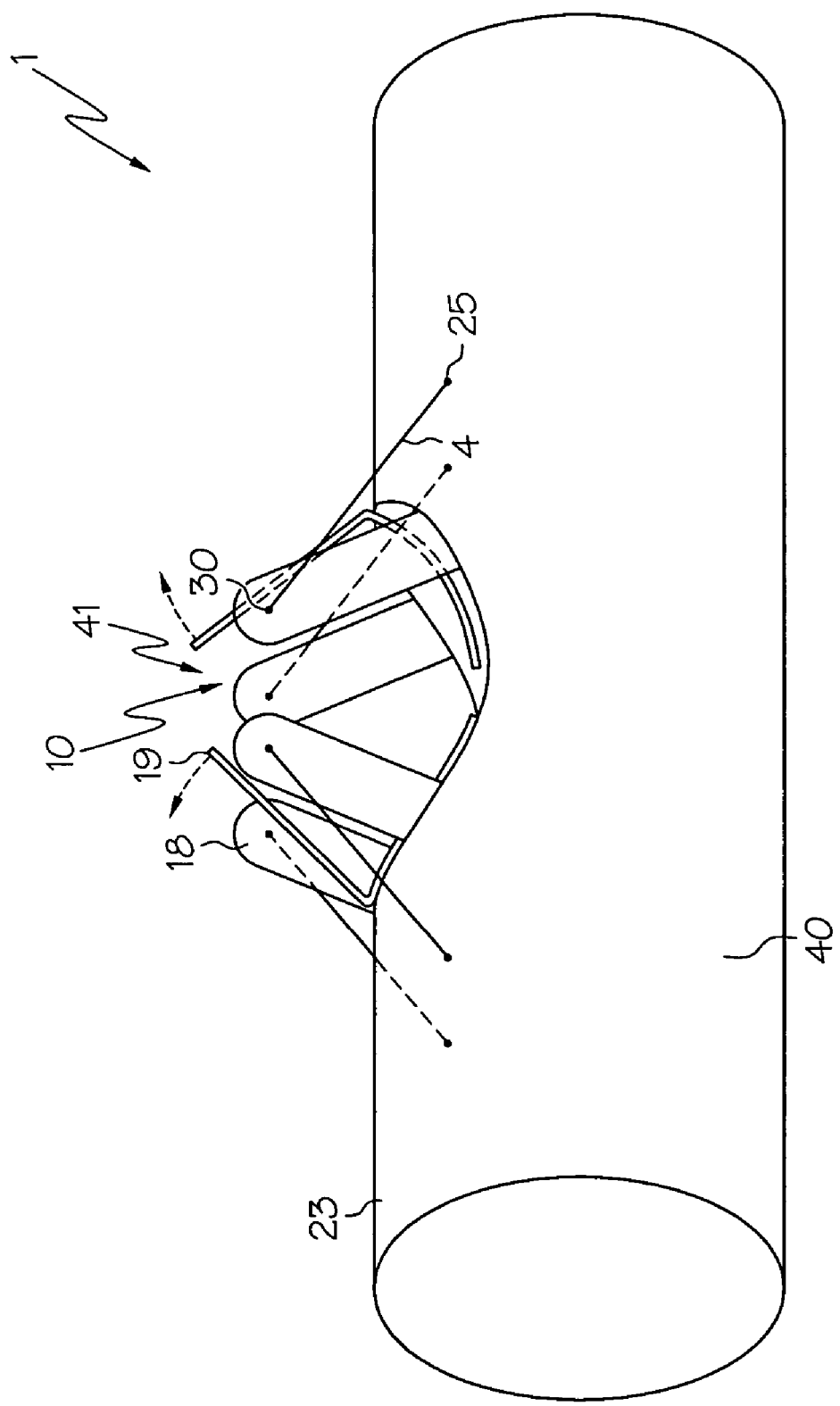
FIG. 9 is a lateral perspective image of a spring loaded expanded tether guided bifurcated stent.

Referring now to FIG. 9 there is shown an embodiment in which some of the branch members (19) are spring loaded. These spring loaded branch members (19) have a pre-loaded state in which they are restrained along or underneath the circumferential plane (23) of the primary stent body (11) until the stent (1) is expanded. Once unrestrained, the spring loaded branch members (19) assume a post loaded state in which they project away from the circumferential plane (23) and form at least part of the secondary fluid lumen (41). In one possible embodiment, the spring loaded branch members (18) are restrained in their pre-loaded state by other overlapping branch members (18) connected by tethers (4) to the primary stent body (11). When the stent (1) expands, the tether connected side branch members (18) are pulled away from the spring loaded side branch members (18) and the spring loaded side branch members (19) transition from a pre-loaded state to a post-loaded state and form at least part of the secondary fluid lumen (41).

Figure 10:
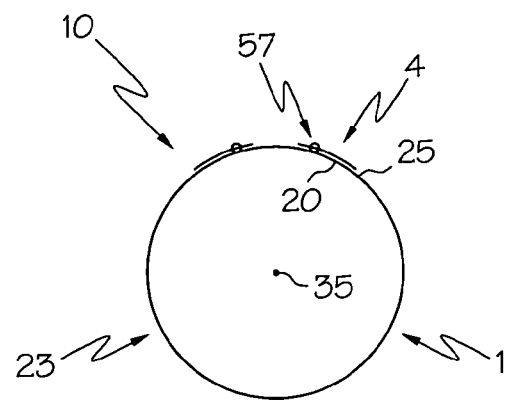
FIG. 10 is a is a cross sectional side perspective image of an unexpanded tether guided bifurcated stent featuring an eyelet tether ring.
Figure 11:
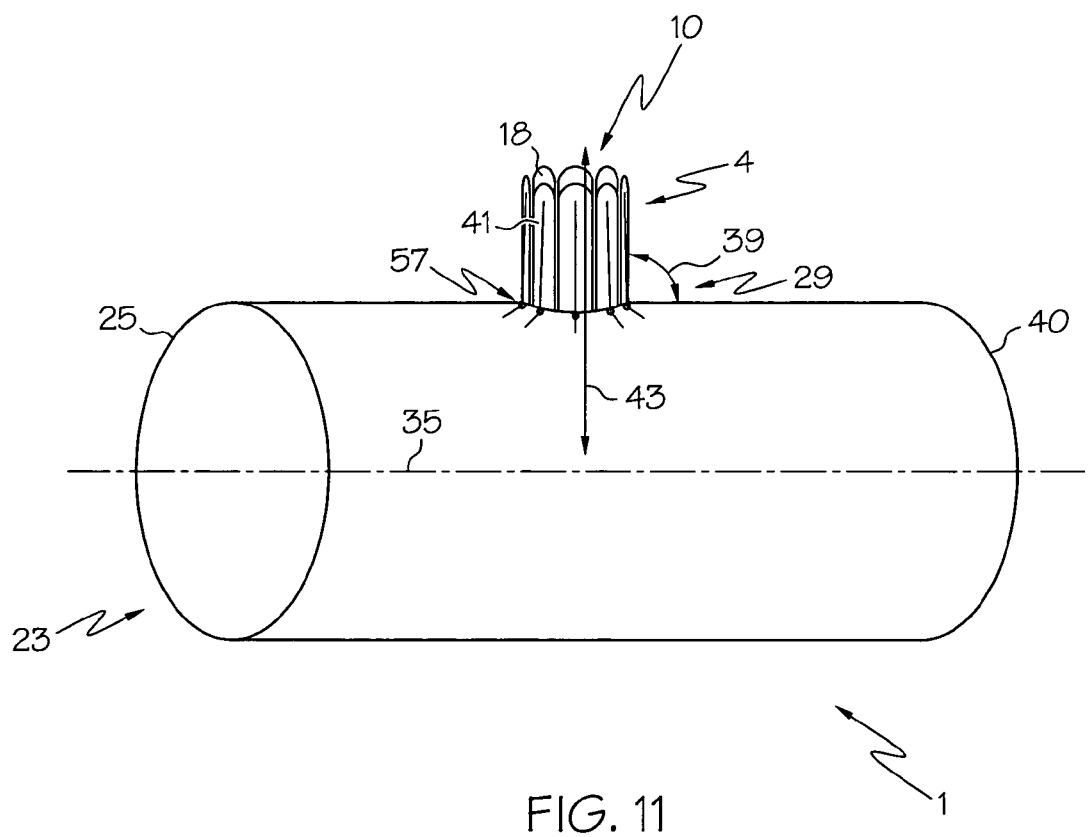
FIG. 11 is a is a cross sectional side perspective image of an expanded tether guided bifurcated stent featuring an eyelet tether ring.

Referring now to FIGS. 10 and 11 there are shown an embodiment in which the tether (4) length runs through an eyelet ring (57). In FIG. 10, the unexpanded stent (1) is shown with the tether (4) extending through an eyelet ring. This ring is a connected to the primary stent body (11) and is located at a position between the first (25) and second (30) ends of the tether. As illustrated in FIG. 11, when the stent is expanded, the stent forms a secondary lumen (41) but unlike in the configuration of FIG. 3, the eyelet rings (57) hold the tethers substantially adjacent to the secondary lumen (41). This reduces the profile of the stent. Although in these illustrations, the eyelet rings are located at the junction of the side branch and the main stent body, the eyelet rings can be positioned anywhere along the stent to provide controlled tether tension.

In some embodiments the stent (1), a delivery system for deploying the stent, or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

These various drawings are representative of the character of the interactions possible between side branch petals and tethers. These drawings are intended solely to facilitate in conveying the inventive concept. The drawings in no way limit the construal of the inventive concept to those inherent in any specific drawings. Similarly, the drawings in no way limit the scope of any claims to those inherent in any specific drawing.

This completes the description of the preferred and alternate embodiments of the invention. The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A bifurcated stent comprising:
   a substantially tubular primary body defining a circumferential plane, an outer surface, a primary lumen and having a primary longitudinal axis extending therethrough, the primary body being expandable from an unexpanded state to an expanded state, wherein in the unexpanded state the primary body has a diameter less than that of the diameter in the expanded state, the primary body comprising a side branch assembly, in the expanded state the side branch assembly comprising a substantially tubular secondary body defining a secondary lumen having a secondary longitudinal axis extending therethrough, the secondary lumen being in fluid communication with the primary lumen, the secondary longitudinal axis forming an oblique angle with the primary longitudinal axis; and
   at least one tether, the at least one tether having a first end, a second end and a length therebetween, the first end engaged to the primary body and a second end engaged to the secondary body, in the unexpanded state, at least a portion of the tether length extending along the circumferential plane of the primary body, in the expanded state at least a portion of the length of the tether moved to a position defining a vector which forms an angle greater than zero with the circumferential plane of the primary body.

2. The stent of claim 1 in which the side branch assembly is constructed of a plurality of interconnected angled members wherein adjacent members are disposed about an opening in the main stent body, the interconnected angled members and the opening define a visibly recognizable petal pattern arrangement.

3. The stent of claim 2 wherein at least one curved angled member is self expanding.

4. The stent of claim 2 wherein at least flap member is self expanding.

5. The stent of claim 2 wherein at least some portion of the curved members have a greater thickness than others.

6. The stent of claim 2 wherein at least some portion of the curved members are more flexible than others.

7. The stent of claim 2 in which the angled members when in the unexpanded state completely cover the opening.

8. The stent of claim 1 in which the side branch assembly is constructed of a plurality of interconnected flap members wherein adjacent members are disposed about an opening in the main stent body, the interconnected flap members and opening define a visibly recognizable flap pattern arrangement.

9. The stent of claim 8 in which the flaps are triangular.

10. The stent of claim 8 in which the flaps are rectangular.

11. The stent of claim 8 in which the flaps are quadrilateral.

12. The stent of claim 8 in which the flaps when in an unexpanded state overlap.

13. The stent of claim 8 wherein at least some portion of at least one flap member has a greater thickness than others.

14. The stent of claim 8 least some portion of at least one flap member has is more flexible than others.

15. The stent of claim 8 in which the flap members when in the unexpanded state completely cover the opening.

16. The stent of claim 1 wherein the oblique angle is about 90 degrees.

17. The stent of claim 1 wherein a balloon assists the tether in adjusting the side branch assembly into its expanded state.

18. The stent of claim 1 wherein the main tubular body of the stent further comprises struts, at least some portion which have a greater thickness than others.

19. The stent of claim 1 wherein the main tubular body of the stent comprises struts, at least some portion which are more flexible than others.

20. The stent of claim 1 further comprising an eyelet ring in which a portion of the tether length between the first tether end and the second tether ends extends through the eyelet ring and the eyelet ring is attached to the bifurcated stent.

* * * * *